US00PP13865P39

(12) United States Plant Patent
Kanno

(10) Patent No.: US PP13,865 P3
(45) Date of Patent: Jun. 3, 2003

(54) OSTEOSPERMUM PLANT NAMED 'KAKEGAWA AU7'

(75) Inventor: Masao Kanno, Chigasaki (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 09/971,628

(22) Filed: Oct. 9, 2001

(65) Prior Publication Data

US 2003/0070198 P1 Apr. 10, 2003

(51) Int. Cl.[7] ..... A01H 5/00

(52) U.S. Cl. ..... Plt./360

(58) Field of Search ..... Plt./360

*Primary Examiner*—Bruce R. Campell
*Assistant Examiner*—Annette Para
(74) *Attorney, Agent, or Firm*—Jondle & Associates PC

(57) ABSTRACT

An Osteospermum plant particularly distinguished by its white and pink flower color and tendency to hold flowers open later in the evening.

1 Drawing Sheet

GENUS AND SPECIES

*Osteospermum fruiticosum.*

VARIETY DENOMINATION

'Kakegawa AU7'.

BACKGROUND OF THE NEW PLANT

The present invention originated in 1984 by a cross between breeding line No. 8 (unpatented), possessing white flowers and breeding line No.16 (unpatented), possessing white flowers and a blue eye. The $F_1$ seed from this cross was sown in Fall, 1984 and in Spring, 1985 two selections were made and the two selected plants were intercrossed. The $F_1$ seed from these two sister lines was sown in Fall, 1985 and in Spring, 1986 six plants were selected for intercrossing. The $F_1$ seed from these six plants was again sown in Fall, 1986. In 1987 a pink flowered selection named No. 131 (unpatented) was made. In 1988 breeding line No. 99 (unpatented) was crossed to No. 131. In 1989 the $F_1$ plant No. 209 (unpatented) was selected for its pale pink flowers and dwarf habit. In 1990, line No. 209 was crossed to line No. 159 (unpatented). In 1991 two $F_1$ plants were selected from this cross for their light pink flower color and tendency to hold flowers open later in the evening and named No. 2127 (unpatented) and No. 237 (unpatented). In 1992 these two plants were crossed to produce $F_2$ seed. In 1993 the $F_2$ plant, G7-683, was selected from the $F_2$ population for its flower color and holding flowers open later. In Fall, 1993 the plant was vegetatively propagated and stability was confirmed in Spring, 1994. The line was established as 'Kakegawa AU7', and determined to have its characteristics firmly fixed.

DESCRIPTION OF PHOTOGRAPH

This new Osteospermum plant is illustrated by the accompanying photograph which shows blooms, and foliage of the plant in full color, the colors shown being as true as can be reasonably obtained by conventional photographic procedures.

DESCRIPTION OF THE NEW CULTIVAR

Figure 1:
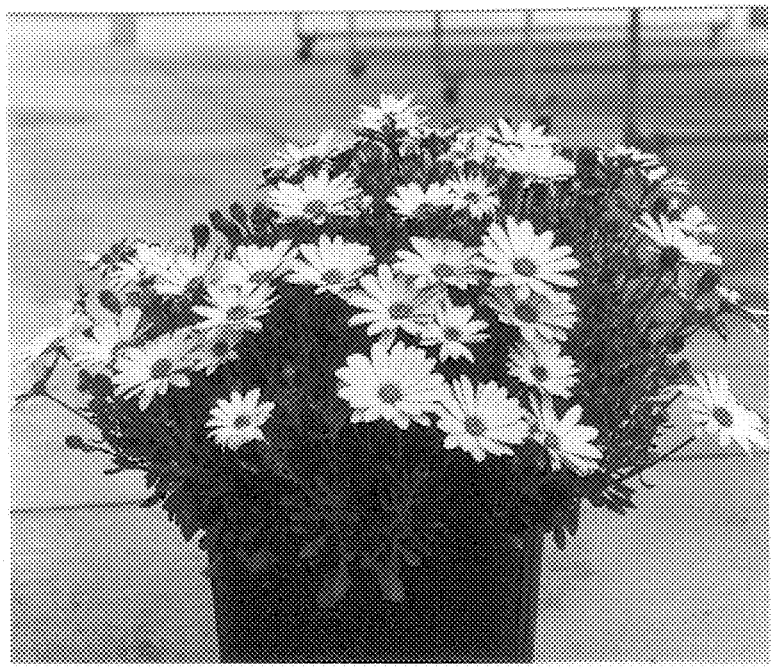
FIG. 1 shows a view of three plants propagated in a 20 cm diameter pot.
Figure 2:
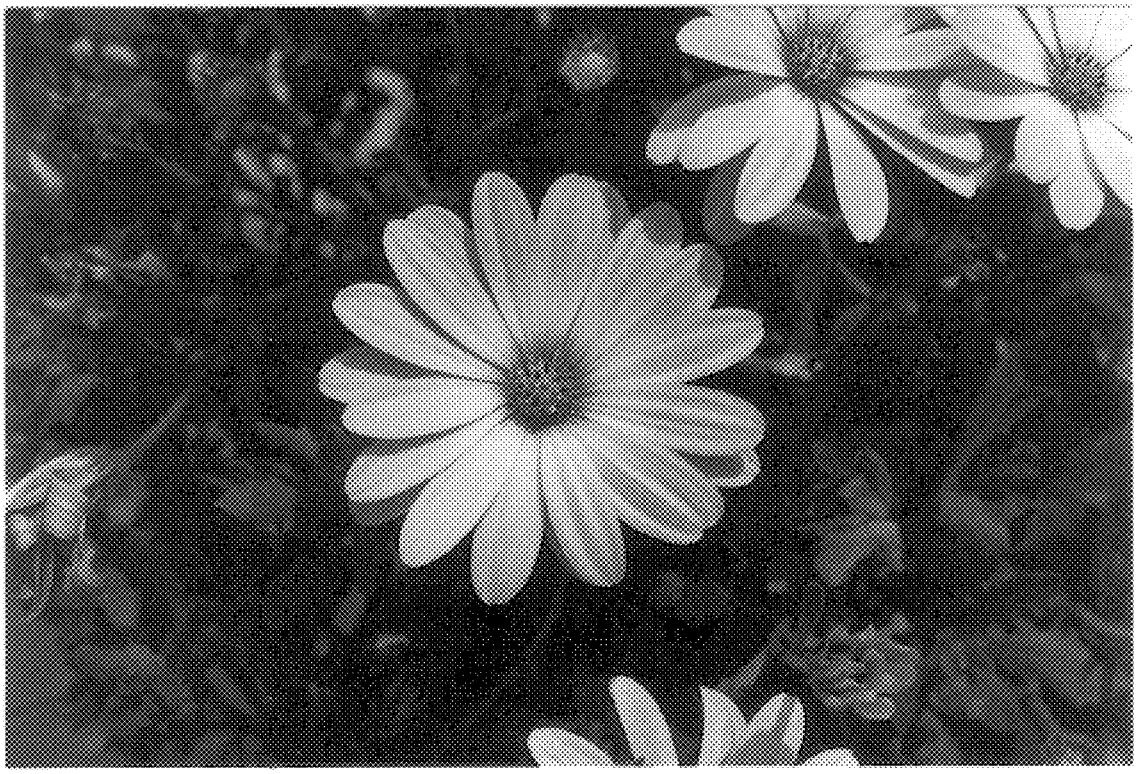
FIG. 2 shows a close-up view of a single inflorescence.

The following detailed descriptions set forth the distinctive characteristics of 'Kakegawa AU7'. The data which defines these characteristics were collected from asexual reproductions carried out in Salinas, Calif. Data was collected on plants 28 weeks from transplanting rooted cuttings into 16 cm diameter pots and growing as described below. Color references are to The R.H.S. Colour Chart of The Royal Horticultural Society of London (R.H.S.).

DESCRIPTION OF THE NEW PLANT

Classification:

*Family.*—Compositae.

*Botanical.*—*Osteospermum fruticosum.*

*Commercial.*—Cape Daisy.

Parentage:

*Female parent.*—Breeding line No. 2127 (unpatented).

*Male parent.*—Breeding line No. 237 (unpatented).

Growth:

*Time to produce a rooted cutting.*—Cuttings will colonize a 2.5 cm diameter by 2.5 cm tall greenhouse tray cell with peat-based plant media in approximately five weeks. Cuttings are dipped in a normal dilution (1:9) of Dip 'N Grow™ root inducing solution in water. The trays are misted hourly during rooting.

*Environmental conditions for plant growth.*—Rooted cuttings are transplanted to pots with a 16 cm diameter, one plant per pot. Peat moss-based growing media is used. The pots are watered using a 150–200 ppm fertilizer solution containing 18% nitrogen, 8% phosphorus and 18% potassium. The soil is allowed to dry between waterings. During the first few weeks after transplanting the plants should have evening temperatures around 15–18° C. for good root growth. When plants reach 7.5–10 cm in height they are pinched back to 5–6 leaves to promote branching. The plants are grown through the winter in cool greenhouses (10–15° C.) with no shading to keep their habit compact. In spring, after the plants have received at least four weeks of cool conditions to vernalize, warmer temperatures can be used to promote blooming. Spring and summer daytime high temperatures in Salinas, Calif., where the data was collected, range from 16–25° C.

*Time to bloom from propagation.*—18–20 weeks when rooted vegetative cuttings are transferred to a 16 cm diameter pot in late Fall and given several weeks of below 50° F. temperature prior to increasingly warmer spring weather.

*Habit.*—Vigorous, well branched.

*Life cycle.*—Perennial.

Plant:

*Form.*—Upright.

*Plant size.*—Height is 35–40 cm; width is 35–40 cm.

Stems:

*Internode length.*—0.8–1.0 cm.

*Color.*—Yellow-green (RHS N144A).

*Description.*—Strong, erect, herbaceous.

*Stem length.*—With pinching stems back to 5 or 6 leaves to promote branching, stems will terminate with petioles at about 10–14 cm.

*Stem diameter.*—2.0–4.0 mm.

*Pubescence.*—Short, transparent.

*Peduncle length.*—12–5 cm.

*Peduncle diameter.*—2–2.5 cm.

*Peduncle color.*—Yellow-green RHS N144A.

Leaves:

*Arrangement.*—Alternate.

*Shape.*—Spatulate.

*Length.*—Up to 7 cm.

*Width.*—Up to 2 cm.

*Apex.*—Mucronate.

*Base.*—Oblique, sessile.

*Margin.*—Serrate.

*Venation.*—Pinnate.

*Color.*—Upper is green (RHS 137A); Lower is green (RHS 137C).

*Venation.*—Upper surface is green RHS 137A; lower surface is green RHS 137C.

Inflorescence:

*Type.*—Capitulum (head); disc florets are staminate and ray florets are carpellate.

*Diameter.*—5.5–6.0 cm.

*Depth.*—2.0–2.5 cm when fully open.

*Disc diameter.*—2.5 cm.

*Lastingness of the individual inflorescence.*—7–10 days.

*Habit.*—Determinate.

*Fragrance.*—None.

*Fruit and seed.*—None.

Phyllaries:

*Description.*—16–21 phyllaries, arranged symmetrically.

*Shape.*—Linear.

*Apex.*—Acute.

*Size.*—Length is 1.0–1.2 cm; Width is 2.0–3.0 mm.

*Margin.*—Entire.

*Color.*—Upper is green (RHS 137D) and lower is green (RHS 138C).

Ray florets:

*Corolla.*—One ray floret per flower on outer whorl of flowers. Only the outer row of florets are the ray florets.

*Ray florets.*—13–24.

*Ray florets size.*—Length of floret is 3.0 cm; width is 0.8 cm.

*Ray florets shape.*—Spatulate.

*Ray florets apex.*—Obtuse with indentation at tip.

*Ray florets margin.*—Entire.

*Ray florets color.*—Ventral surface of ray florets is white with shades of red-purple (RHS N74C) at the tip and solid purple (RHS 77B) at the base. Dorsal surface of ray florets is purple-violet (RHS N81A) with green-yellow (RHS 1C).

*Ovary.*—Inferior.

*Style form.*—One style with two stigma branches.

*Style color.*—Yellow (RHS 4D).

*Stigma color.*—Purple-violet (RHS N82A).

*Pistil.*—One per ray floret.

*Pistil length.*—5 mm.

Inflorescence bud:

*Bud shape.*—Tubular.

*Bud size.*—Length is 5 mm and width is 1 mm.

*Color of bud tip.*—Violet-blue (RHS N92B).

Disc florets:

*Number per head.*—80–85.

*Disc florets shape.*—Tubular.

*Disc florets length.*—5 mm at bud stage; 7 mm at mature floret.

*Disc florets width.*—1 mm.

*Disc florets apex.*—Rounded.

*Disc florets color.*—Without dissecting the florets from the inflorescence head, they are violet-blue RHS N92B at bud stage; purple RHS N77A when anthers emerge and yellow-orange RHS 17A when anthers shed pollen.

*Anther color.*—Purple (RHS N77A).

*Filament color.*—Yellow (RHS 4D).

*Pollen color.*—Yellow-orange (RHS 17A).

Disease and Insect Resistance

No susceptibility to diseases or insects noted to date.

Comparison with Known Cultivars

'Kakegawa AU7' is most similar to the variety 'Kakegawa AU2', the subject of U.S. Plant patent application Ser. No. 09/657,540 which is marketed under the name 'Sea Mist Pink and White'. The two plants differ in that 'Kakegawa AU7' has ray florets that are predominately white in color with a small area of bluish violet at the base of the floret surrounding the disc while the ray florets of 'Kakegawa AU2' are predominately pink with the basal third white in color. Table 1 compares the differences between the two plants.

TABLE 1

| Characteristic | 'Kakegawa AU7' | 'Kakegawa AU2' |
|---|---|---|
| Ray florets | White ray floret with shades of red-purple (N74C) at the tip and purple (77B) at the base | Red-purple (70B) ray florets with white (155) at the base |

TABLE 1-continued

| Characteristic | 'Kakegawa AU7' | 'Kakegawa AU2' |
|---|---|---|
| Veins on dorsal surface of ray floret | Green-yellow (1C) | Violet-purple (83B) |

When 'Kakegawa AU7' is compared to parental lines 2127 and 237 the most predominant difference is that line 2127 and 237 both have light pink ray florets and they stay open in the evening.

I claim:

1. A new and distinct plant of Osteospermum as shown and described herein.

* * * * *